US011690633B2

(12) United States Patent
Min et al.

(10) Patent No.: US 11,690,633 B2
(45) Date of Patent: Jul. 4, 2023

(54) LEFT ATRIAL APPENDAGE OCCLUDER DEVICE

(71) Applicant: CORNELL UNIVERSITY, Ithaca, NY (US)

(72) Inventors: James K. Min, Brooklyn, NY (US); Simon Dunham, New York, NY (US); Bobak Mosadegh, New York, NY (US); Sanlin S. Robinson, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/729,699

(22) Filed: Apr. 26, 2022

(65) Prior Publication Data

US 2022/0249101 A1 Aug. 11, 2022

Related U.S. Application Data

(63) Continuation of application No. 16/319,303, filed as application No. PCT/US2017/043247 on Jul. 21, 2017.

(Continued)

(51) Int. Cl.
*A61B 17/12* (2006.01)
*A61L 31/06* (2006.01)
(Continued)

(52) U.S. Cl.
CPC .. *A61B 17/12195* (2013.01); *A61B 17/12122* (2013.01); *A61B 17/12136* (2013.01);
(Continued)

(58) Field of Classification Search
CPC ........ A61B 17/12172; A61B 17/12022; A61B 17/12122; A61B 17/12136;
(Continued)

(56) References Cited

U.S. PATENT DOCUMENTS

| 2002/0022860 A1 | 2/2002 | Borillo et al. |
| 2003/0023266 A1* | 1/2003 | Borillo ............ A61B 17/12172 606/200 |

(Continued)

FOREIGN PATENT DOCUMENTS

| CN | 1342056 | 3/2002 |
| WO | WO-00/27292 A1 | 5/2000 |
| WO | WO-2015/164836 A1 | 10/2015 |

OTHER PUBLICATIONS

Michael Hwai Ren Chang, "Application of Numerical Simulation in Cardiovascular Medicine", Feb. 2015, pp. 117. (Year: 2015).*

(Continued)

*Primary Examiner* — Richard G Louis
*Assistant Examiner* — Chima U Igboko
(74) *Attorney, Agent, or Firm* — Foley & Lardner LLP

(57) ABSTRACT

The present disclosure describes a device that can be implanted into the left atrial appendage for occlusion. The device can prevent or reduce thrombus formation in this anatomic region for patients with atrial fibrillation. This device includes a patient-specific inflatable device that represents a patient's anatomy or morphological class. The inflatable device can be designed by imaging (e.g., computed tomography, magnetic resonance imaging) the patient's anatomy. Through a catheter (or surgically), the inflatable device can be filled with an inflation fluid to occlude the appendage in a patient-specific fashion.

20 Claims, 8 Drawing Sheets

Related U.S. Application Data

(60) Provisional application No. 62/365,460, filed on Jul. 22, 2016.

(51) Int. Cl.
*A61L 31/18* (2006.01)
*A61B 17/00* (2006.01)
*A61B 90/00* (2016.01)

(52) U.S. Cl.
CPC ............... *A61L 31/06* (2013.01); *A61L 31/18* (2013.01); *A61B 2017/005* (2013.01); *A61B 2017/00632* (2013.01); *A61B 2090/374* (2016.02); *A61B 2090/378* (2016.02); *A61B 2090/3762* (2016.02)

(58) Field of Classification Search
CPC .......... A61B 17/1219; A61B 17/12195; A61B 34/10; A61B 2017/005; A61B 2017/00632; A61B 2090/374; A61B 2090/3762; A61B 2090/378; A61B 2034/108; A61L 31/06; A61L 31/18
See application file for complete search history.

(56) References Cited

U.S. PATENT DOCUMENTS

| | | |
|---|---|---|
| 2005/0288706 A1 | 12/2005 | Widomski et al. |
| 2012/0271337 A1 | 10/2012 | Figulla et al. |
| 2012/0323267 A1 | 12/2012 | Ren |
| 2013/0018413 A1 | 1/2013 | Oral et al. |
| 2014/0018841 A1 | 1/2014 | Peiffer et al. |
| 2014/0100596 A1 | 4/2014 | Rudman et al. |
| 2014/0277074 A1 | 9/2014 | Kaplan et al. |
| 2015/0196305 A1 | 7/2015 | Meyer et al. |
| 2016/0166242 A1 | 6/2016 | Krishnan |
| 2016/0371838 A1* | 12/2016 | Neetz ..................... A61B 34/10 |
| 2017/0042550 A1* | 2/2017 | Chakraborty .... A61B 17/12031 |

OTHER PUBLICATIONS

Final Office Action in U.S. Appl. No. 16/319,303 dated Feb. 16, 2021.
Final Office Action on U.S. Appl. No. 16/319,303 dated Jul. 19, 2022.
Foreign Action on CN 201780058389.7 dated Sep. 17, 2021.
Foreign Action on EP 17831939.8 DTD Mar. 9, 2022.
International Search Report and Written Opinion, PCT/US2017/043247 (dated Oct. 10, 2017).
Non-Final Office Action in U.S. Appl. No. 16/319,303 dated Jul. 17, 2020.
Non-Final Office Action on U.S. Appl. No. 16/319,303 dated Nov. 2, 2021.
Partial Supplementary European Search Report in EP Patent No. 17831939.8 dated Feb. 3, 2020 (10 pages).

* cited by examiner

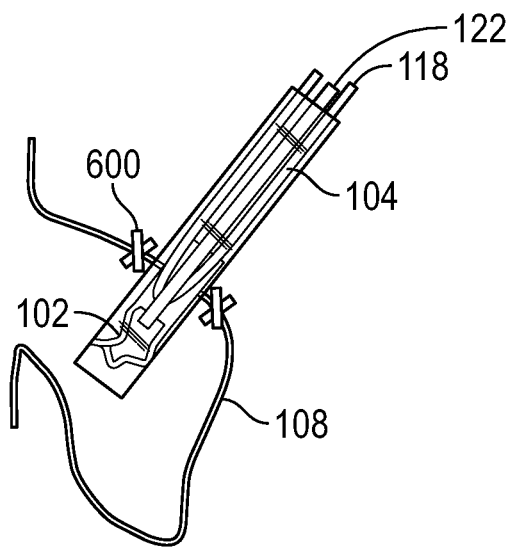
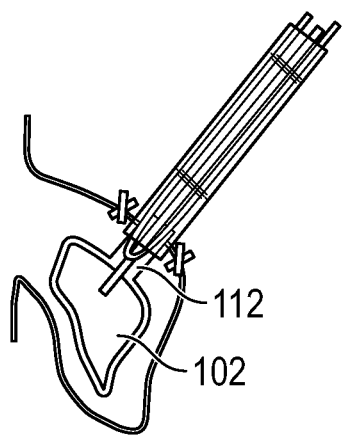
FIG. 6A       FIG. 6B
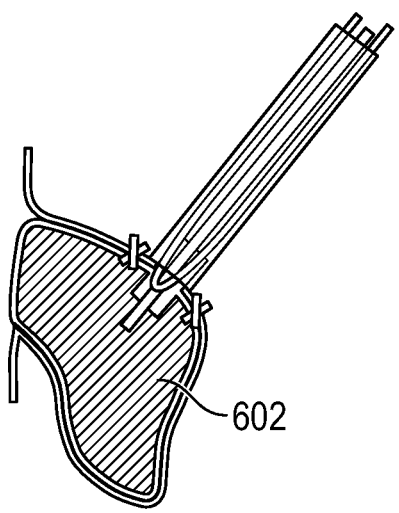
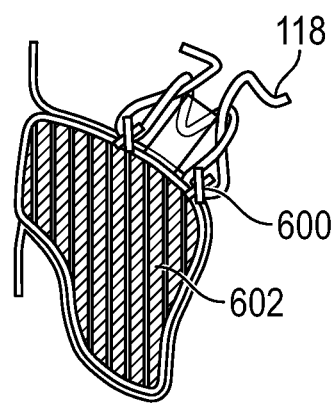
FIG. 6C       FIG. 6D

LEFT ATRIAL APPENDAGE OCCLUDER DEVICE

CROSS-REFERENCE TO RELATED APPLICATIONS

This application is a continuation of U.S. patent application Ser. No. 16/319,303, filed Jan. 18, 2019, which is a National Stage Application of PCT/US2017/043247, filed Jul. 21, 2017, which claims the benefit of and priority to U.S. Provisional Patent Application No. 62/365,460, filed Jul. 22, 2016, the entire contents of which are incorporated herein by reference.

BACKGROUND OF THE DISCLOSURE

Stroke is one of the leading causes of death and disability in the United States. Atrial fibrillation (AF), which promotes the formation of blood clots, increasing the risk for stroke 5 to 7 times compared to the general population. The use of warfarin or oral anti-coagulant, is currently the mainstay of treatment for reducing the risk of stroke due to AF. This therapy, however, is systemic and increases the risk of bleeding dramatically. Therefore, alternative treatments that locally prevent the development of thrombi in the atrium are desirable. It has been documented that the left atrial appendage (LAA) is the source for more than 90% of thrombi in patients with non-rheumatic AF. The LAA is a small sac in the muscle wall of the left atrium, and blood may become stagnant and clot when the atrium does not effectively contract; stroke occurs when these clots are pumped out of the heart and into the brain.

SUMMARY OF THE DISCLOSURE

The occluder device described herein enables the occlusion of the LAA with a non-pharmacologic alternative to anticoagulant medications. The occlusion of the LAA can reduce the likelihood of stroke in patients with AF. The present disclosure describes a system and method for sealing the LAA and reducing the risk of clot formation. The present system can seal the LAA to prevent leakage of blood and dislodgement of the device, which can reduce the need for the continual treatment of the patient with anti-coagulants. In some implementations, the present system provided a better seal by providing a patient-specific occluding device.

According to at least one aspect of the disclosure, an implantable, patient- or morphology-specific occluder device includes an inflatable implant. The inflatable implant includes a first lobe and a second lobe. A volumetric shape of the inflatable implant in an inflated state is configured to match a LAA morphology class. The inflatable implant can include a valve that is configured to enable a lumen to pass into an interior volume of the inflatable implant. The lumen can pass through the valve in a first direction. The valve can substantially prevent an inflation fluid from flowing in a second direction that is opposite the first direction. The inflatable implant can include the inflation fluid. The inflation fluid can be configured to fill the interior volume of the inflatable implant to expand the inflatable implant from a contracted (also referred to as a deflated stated) state to the inflated state.

In some implementations, the valve can include a polymeric septum that is configured to seal a location pierced by the lumen. The inflation fluid can be a curable fluid. The inflation fluid can be configured to cure upon an exposure to one of an ultraviolet energy or a thermal energy. The inflation fluid can include at least one of an epoxy, polyethylene glycol, or a collagen-based polymeric gel. The inflation fluid can include at least one of saline and a self-expanding foam. The LAA morphology class can be one of a chicken wing class, a cactus class, or a cauliflower class.

In some implementations, the first lobe can include a first volumetric shape and the second lobe can include a second volumetric shape that is different than the first volumetric shape. The inflatable implant can include a third lobe. The inflatable implant can include the first lobe with a first axis and the second lobe with a second axis that is askew from the first axis.

According to at least one aspect of the disclosure, a method to occlude an atrial appendage can include deploying an inflatable implant into a LAA. The inflatable implant can include a first lobe and a second lobe. A volumetric shape of the inflatable implant in an inflated state can be configured to match a LAA morphology class. The inflatable implant can include a valve that is configured to enable a lumen to pass into an interior volume of the inflatable implant in a first direction and substantially prevent an inflation fluid from flowing in a second direction that is opposite the first direction. The method can include filling the inflatable implant with the inflation fluid. The inflation fluid can be configured to fill the interior volume of the inflatable implant to expand the inflatable implant from a contracted state to the inflated state. The method can include anchoring the inflatable implant to a wall of the LAA.

In some implementations, the method can include removing the lumen from the valve. The valve can include a polymeric septum that is configured to seal a location pierced by the lumen. The method can include curing the inflation fluid. The inflation fluid can be cured by exposing the inflation fluid to at least one of an ultraviolet energy or a thermal energy. The inflation fluid can include at least one of an epoxy, polyethylene glycol, or a collagen-based polymeric gel. The inflation fluid can include at least one of saline and a self-expanding foam. The LAA morphology class can be one of a chicken wing class, a cactus class, or a cauliflower class. The first lobe can include a first volumetric shape and the second lobe can include a second volumetric shape that is different than the first volumetric shape. The inflatable implant can include a third lobe. The inflatable implant can include the first lobe with a first axis and the second lobe with a second axis that is askew from the first axis.

BRIEF DESCRIPTION OF THE DRAWINGS

The figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, and emphasis is instead being placed upon illustrating the principles of the teachings. The drawings are not intended to limit the scope of the present teachings in any way. The system and method may be better understood from the following illustrative description with reference to the following drawings in which:

FIGS. 5A-6D illustrate example methods for implanting a morphology-specific occluder device.

DETAILED DESCRIPTION

The various concepts introduced above and discussed in greater detail below may be implemented in any of numerous ways as the described concepts are not limited to any particular manner of implementation. Examples of specific implementations and applications are provided primarily for illustrative purposes.

Figure 1:
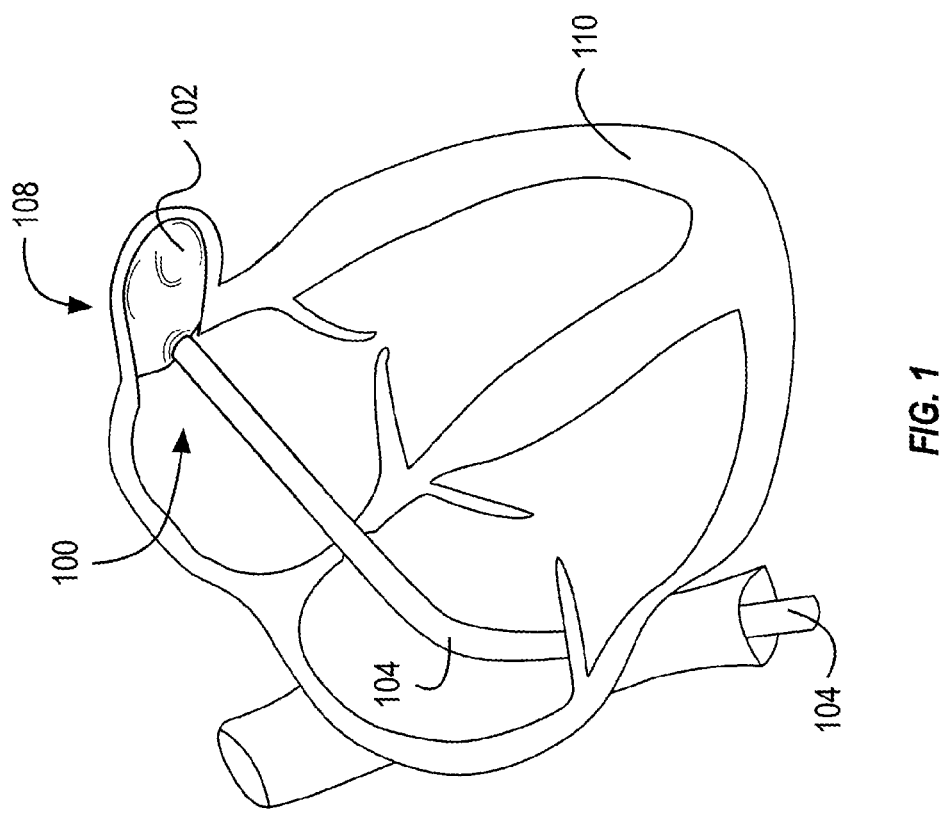
FIG. 1 illustrates an example occluder system within the heart of a patient.

FIG. 1 illustrates an example occluder system 100 within the heart 110 of a patient. The occluder system 100 includes an occluder device 102 that can be deployed through a catheter 104. The occluder device 102 can also be referred to as a morphology-specific occluder (MSO) device 102. The MSO device 102 can be deployed from the catheter 104 and into the LAA 108 of the heart 110. Once deployed, the MSO device 102 can be anchored to the LAA 108 and detached from the catheter 104. In some implementations, the system 100 is a surgical or other kit that includes the MSO device 102 and catheter 104.

The MSO device 102 can be configured, selected, or manufactured for the patient into whom the MSO device 102 is implanted. The MSO device 102 can be an inflatable balloon implant with a geometry that substantially matches the anatomical morphology of the patient's LAA 108. The MSO device 102 can include a plurality of lobes that when inflated substantially match the LAA shape of a specific patient or the shape of a LAA morphology class. As described below, the morphology of the patient's LAA 108 can be ascertained by non-invasive computed tomography (CT) imaging. The MSO device 102 can be non-spherical when inflated. The MSO device 102 can have a number of advantages over a spherical balloon shape. While a spherical balloon-shaped device that is composed of soft materials can conform to most shapes, the spherical device may need to be over-inflated to fill the patient's LAA 108. The inflation of the spherical device can induce strain on both the elastomeric material of the spherical device, the multi-lobular LAA structures, and the tissue surrounding the LAA. Over-inflation of a spherical device to obtain full occlusion could also compress the circumflex artery that runs underneath the LAA. In some implementations, the MSO device 102 can be manufactured for a specific patient. In some implementations, the morphology of the patient's LAA 108 can be categorized into a class and a specific shape of the MSO device 102 can be selected based on the class.

The MSO device 102 is configured to occlude the patient's LAA. In other implementations, the MSO device 102 is configured to occlude other portions of the patient's heart. For example, the MSO device 102 can be used in patent ductus arteriosus closures, atrial septal defect closures, and heart valve repairs.

The catheter 104 is configured for insertion at a patient's femoral artery. The tip of the catheter 104 is advanced through a patient's arterial system toward the patient's LAA. The catheter 104 includes an elongate flexible body that can include PET, nylon, polyethylene, polyether ether ketone, or any combination thereof. In some implementations, the catheter 104 is configured for insertion through a laparoscopic or other surgical opening to be advanced toward the outer surface of the LAA 108.

In some implementations, the catheter 104 has a length between about 50 cm and about 150 cm. In some implementations, the outer diameter of the catheter 104 is between about 0.2 mm and about 6 mm, between about 0.5 mm and about 5 mm, between about 0.5 mm and about 4 mm, and between about 1 mm and about 3 mm. The catheter 104 can have a French size between about 14 and about 22, between about 14 and about 20, or between about 16 and about 18. In some implementations, the catheter 104 includes a solid core to enable the deployment tip of the catheter 104 to be controlled. For example, the core can include a stainless steel, nitinol, nickel titanium alloy, or polymeric materials that can be rotated by the surgeon to control the rotation of the catheter 104. In some implementations, the catheter 104 includes radiopaque to enable the surgeon to visualize the placement of the catheter 104 within the patient with the use of X-ray imaging. In some implementations, the catheter 104 includes an inflatable balloon. The inflatable balloon is configured to inflate and at least partially block the LAA during the deployment of the MSO device 102.

Figure 2B:
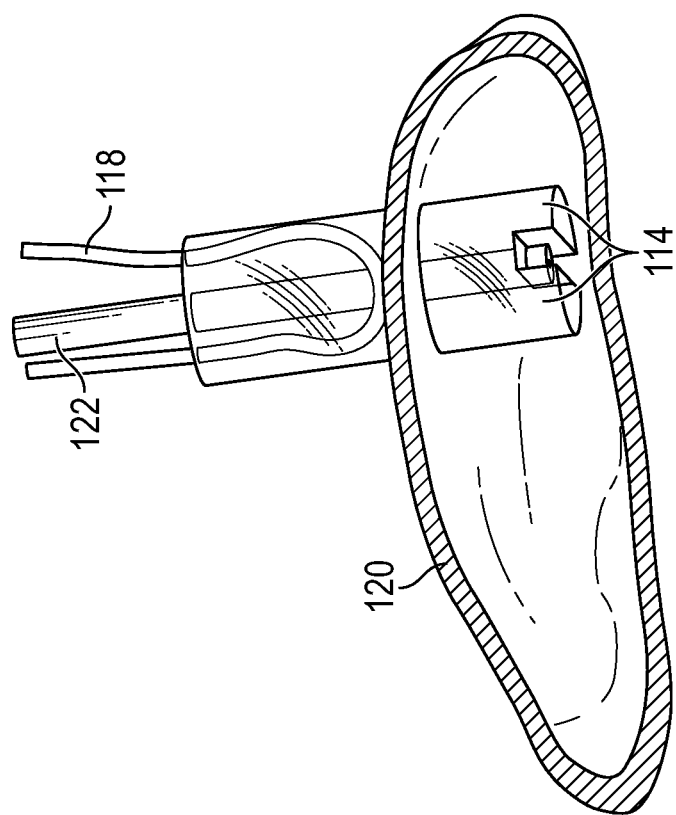
FIG. 2B illustrates a cross-sectional view of the example morphology-specific occluder device illustrated in FIG. 2A.
Figure 2A:
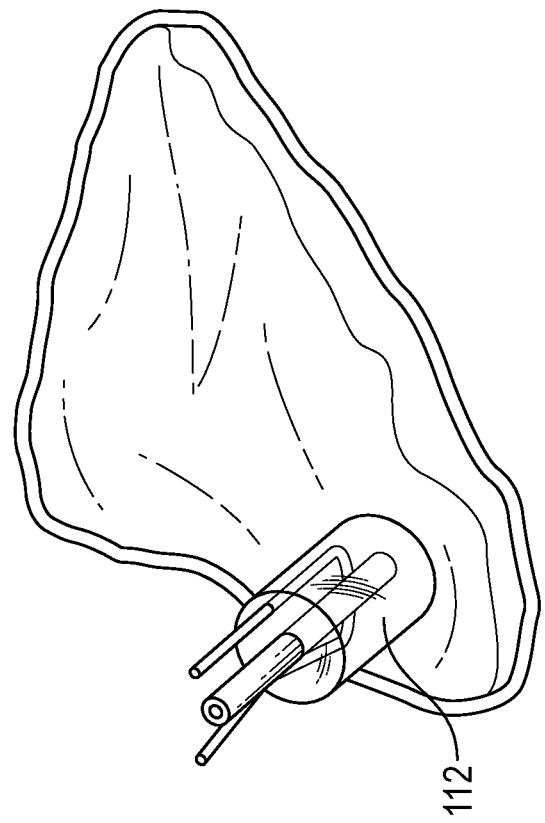
FIG. 2A illustrates an example morphology-specific occluder device for use in the example occluder system illustrated in FIG. 1.

FIG. 2A illustrates an example MSO device 102. FIG. 2B illustrates a cross-sectional view of the example MSO device 102 in an inflated state. The inflated state can be any state where the MSO device 102 is expanded with respect to the configuration of the MSO device 102 prior to deployed (e.g., when the MSO device 102 is within the catheter 104). The MSO device 102 can be expanded or otherwise inflated with a fluid, gas, foam, or other material. In some implementations, the MSO device 102 can be self-expanding. For example, the walls of the MSO device 102 can include nitinol ribs that deploy to an expanded state once the MSO device 102 is deployed from the catheter 104.

The MSO device 102 includes a valve 112 through which the MSO device 102 can be filled. The valve 112 can enable a lumen 122 to be inserted in a first direction and into an interior space of the MSO device 102 but substantially prevents fluid from flowing in the opposite direction. The MSO device 102 can be monolithically integrated with the valve 112. The valve 112 can enable a surgeon to fill the MSO device 102 without leakage once disengaged from the catheter 104. The MSO device 102 can be filled with a hardening material to stabilize the MSO device 102 within the LAA 108 after implantation. The fluid to inflate the MSO device 102 can be passed to the interior of the MSO device 102 via a lumen 122. In some implementations, the lumen 122 is inserted through the valve 112 during the MSO device's non-deployed state (e.g., when the MSO device 102 is in the catheter 104).

The valve 112 can be monolithically integrated into the MSO device 102 during the molding process. Monolithically integrating the valve 112 with the MSO device 102 can enable the MSO device 102 to be inflated to a high pressure without delamination of the valve 112 from its walls of the MSO device 102. The valve 112 can include a polymeric septum that is pierced by lumen 122. Once the MSO device 102 is deployed and secured in the LAA 108, the lumen 122 can be retracted. The polymeric septum valve can seal the location where the lumen 122 previously pierced the septum, sealing the interior of the MSO device 102. The valve 112 can also include a cured material (e.g., a quick setting epoxy can be applied to the opening left by the retracted lumen 122). The valve 112 can include a mechanical valve that is opened to fill the MSO device 102 and then closed once the MSO device 102 is filled.

The valve 112 can include wings 114. The wings 114 are coupled to the internal side of the valve 112 to protect the opposing wall of the MSO device 102 from being pierced accidentally by the lumen 122 during deployment or the filling of the MSO device 102. A portion 116 of the valve 112 can extend past the walls of the MSO device 102. The portion 116 can include attachment anchors 118, which can be sutures. The attachment anchors 118 can be used to secure and anchor the MSO device 102 to the LAA 108. The portion 116 of the MSO device 102 can extend to enable a surgeon to maintain contact with the MSO device 102 throughout the entire implantation procedure. In some implementations, the attachment anchors 118 can be coupled with an outer surface of the wall 120. When positioned on the outer surface of the wall 120, the attachment anchors 118 can come into contact with the inner tissue surface of the LAA 108. The attachment anchors 118 can be surface features such as, but not limited to, ridges, protrusions, barbs, anchors, needles, or other structures that can increase the friction between the MSO device 102 and the LAA 108. The attachment anchors 118 can also include bonding agents. For example, an adhesive or protein bonding agent can be applied to the outer surface of the wall 120 and coupled the MSO device 102 with the LAA 108.

The thickness of the MSO device 102 walls 120 can be between about 0.1 mm about 1 mm, between about 0.2 mm and about 0.8 mm, between about 0.4 mm and about 0.6 mm, or between about 0.5 mm and about 0.6 mm. In some implementations, the MSO device 102 of the occluder system 100 can be fabricated using rapid prototyping techniques, such as direct 3D printing of polyurethane materials or molded from 3D printed templates of silicone materials. These materials can have a wide range of stiffness (ranging from kPa to tens of MPa) and extensibilities (e.g., up to 700%). In some implementations, the material used to fabricate the MSO device 102 is intrinsically soft (as to not damage the heart and to not impede contractions of the heart muscle), but robust enough to withstand the forces exerted on the device when implanted. In some implementations, the MSO device 102 of the occluder system 100 can include polyurethane, silicone, nylon, PET, or a combination thereof. In some implementations, the walls 120 (or other components of the MSO device 102) can include a non-stretchable polymer, such as polyethylene terephthalate (PET), polytetrafluoroethylene (PTFE), nylon, or polyvinyl chloride (PVC). In some implementations, the walls 120 of the MSO device 102 can be reinforced with fabric, metal mesh or wire, or other materials.

For example, the MSO device 102 can be manufactured using a mold that includes both a hard portion (Veroclear, Stratasys) and soft portion (Tango+, Stratasys). One mold can be manufactured for each side of the MSO device 102. Each mold can be filled with a homogenous silicone blend of 69 wt % Dragon Skin®20 (DS20; Smooth-On, Inc.), 10.3 wt % Silicone Thinner® (Smooth-On, Inc.), and 20.7 wt % Sylgard®184 mixture. The silicone blend and molds can then be baked in an oven at 100° C. for 35 minutes. Next, the partially cured silicone blend can be removed from the molds. The two halves of the MSO device 102 can be aligned and bonded together by with DS20 pre-polymer. The coupled halves can be returned to the oven at 100° C. for one hour. Pure DS20 can be used instead of the silicone blend for the seams because the pure DS20 has a higher viscosity and stays in position after placement on the seam. Once fully cured and cooled, the MSO device 102 can be plasma treated and soaked in 12 vol % 3-glycidoxypropyltrimethoxysilane (GPTS; Sigma Aldrich) for one hour. After cleaning and drying the occluder, the MSO device 102 can be rinsed in a solution of −10 wt % PCU in dimethylacetamide (DMAC; Sigma Aldrich). The MSO device 102 can be baked in an oven at 70° C. for 2 hours, and then dipped again into the PCU solution. The MSO device 102 can be placed in a 70° C. oven overnight to fully cure the PCU surface coating. In some implementations, other injection molding processes can be used to manufacture the MSO devices described herein.

The materials of the MSO device 102 are biocompatible. In some implementations, the outer surface of the MSO device 102 is configured to enable endothelialization. For example, the surface of the MSO device 102 facing the left atrium can be covered by endothelial cells approximately 45 days after implantation. This can effectively create a wall between the left atrium and the MSO device 102.

FIGS. 3A-3D illustrate different, class-specific configurations of the MSO device 102. The MSO device 102 can be designed in response to non-invasive computed tomography (CT) imaging, magnetic resonance imaging, or other imaging techniques. For example, 3D renderings of the CT images can be segmented to produce a solid structure of a patient's LAA 108. When manufactured and deployed, the class-specific (or patient specific) MSO device 102 can substantially seal or otherwise fill the LAA 108. In some implementations, the MSO device 102 can be manufactured in different shape templates. The shape templates can match the different morphology classes of the LAA 108. The shape templates can be categorized into four LAA shapes. The shape templates can include, but are not limited to, a cactus shape, a chicken wing shape, a windsock shape, and a cauliflower shape. The type of shape in a patient scan can be automatically detected and the corresponding shape template will be transformed and fitted to the LAA boundary using machine learning techniques. By designing balloons that fit snugly to the complex geometries of the LAA, both the risk of leakage and dislodgement are reduced. The morphology class can also be a patient-specific morphology class. The patient-specific morphology class shape is designed to match the patient's specific anatomy. Each MSO device 102 with a patient-specific morphology class shape can be a custom manufactured MSO device 102. The custom manufactured MSO 102 device can be manufactured to match and substantially fill the LAA of the patient.

Figure 3B:
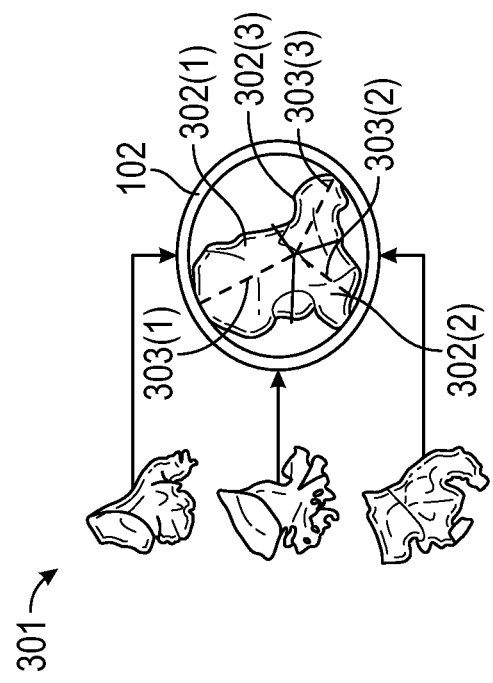
FIGS. 3A-3D illustrate a plurality of human LAA morphologies and different classes of morphology-specific occluder devices for use in the example occluder system illustrated in FIG. 1.
Figure 3D:
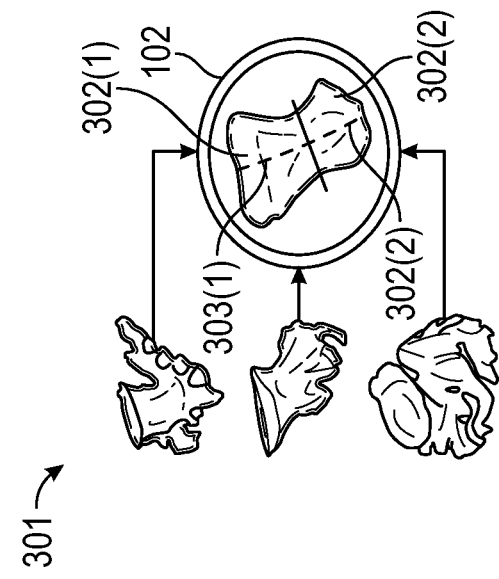
Figure 3A:
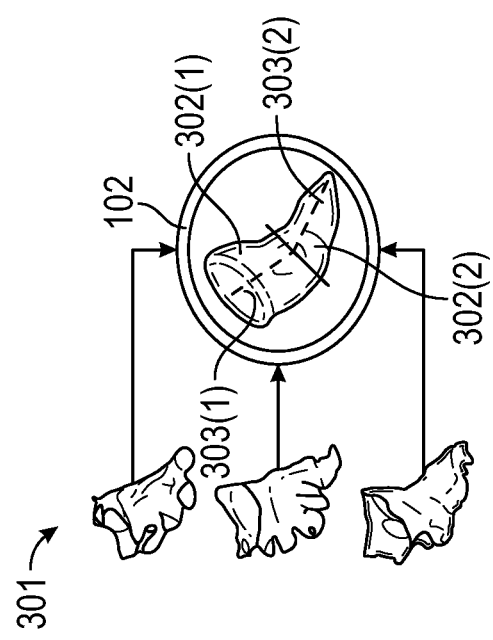
Figure 3C:
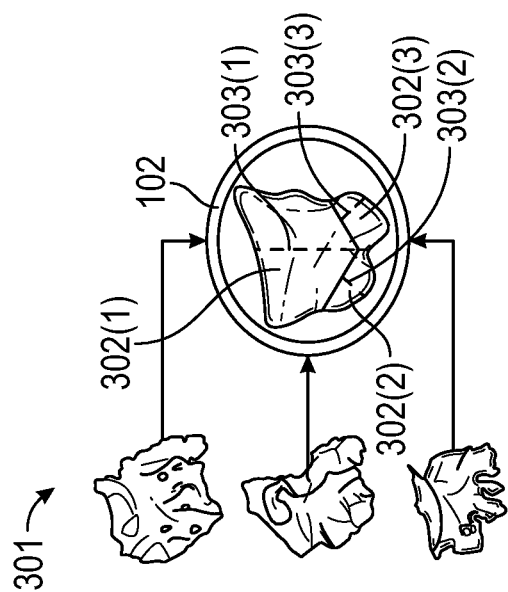

FIGS. 3A-3D illustrate a plurality of human LAA 108 morphologies 301. The morphologies 301 were captured using non-invasive CT imaging. The morphologies 301 were categorized into different classes. Each of the morphologies 301 can include a plurality of lobes. The template shapes of the MSO device 102 can include one or more lobes 302. For example, the MSO device 102 can include between 1 and about 5 lobes. Each of the lobes can have a central axis 303. The lobes 302 can project in different directions such that the axis 303 of each lobe 302 is askew from the other axes 303. FIG. 3A illustrates a plurality of morphologies 301 that are categorized into a windsock class. The MSO device 102 illustrated in FIG. 3A is configured in the windsock template shape. The windsock template shape can include two lobes 302. FIG. 3B illustrates a plurality of morphologies 301 that are categorized into a cactus class. The MSO device 102 illustrated in FIG. 3B is configured in the cactus template shape. The cactus template shape can include three lobes 302. FIG. 3C illustrates a plurality of morphologies 301 that were categorized into a cauliflower class. The MSO device 102 illustrated in FIG. 3C is configured in the cauliflower template shape. The cauliflower template shape can include three lobes 302. The lobes 302 of the cauliflower template shape can include a larger, primary lobe and two secondary lobes. FIG. 3D illustrates a plurality of morphologies 301 that were categorized into a chicken wing class. The MSO device 102 illustrated in FIG. 3D is configured in the chicken wing template shape. The chicken wing template shape includes two lobes 302. The angle between the axes 303 in the windsock template can be greater than that of the angle between the axes 303 in the template chicken wing shape. A template for each of the classes can be generated by determining the overlap of each of a plurality of morphologies 301 within a respective class. In some implementations, the chicken wing template class can include main lobe that is about 1-6 cm long and the angle between the axes 303 of the main lobe and a second lobe can be less than about 100°. In some implementations, the chicken wing template includes a single, main lobe that is greater than 4 cm and is folded at an angle less than about 100°, which can be referred to as a folded-lobe. The windsock template class can include a main lobe that is about 1-6 cm long and the angle between the axes 303 of the main lobe and a second lobe can be greater than about 100°. In some implementations, the windsock template includes a single, main lobe that is greater than 4 cm and is folded at an angle greater than about 100°, which can be referred to as a folded-lobe. The cactus template class can include a main lobe that is between about 1-6 cm long and includes more than two secondary lobes that are each longer than about 0.5 cm or longer than about 1 cm. The cauliflower class template can include a main lobe that is about 1-6 cm long and one or more secondary lobes that are not forked.

Figure 4A:
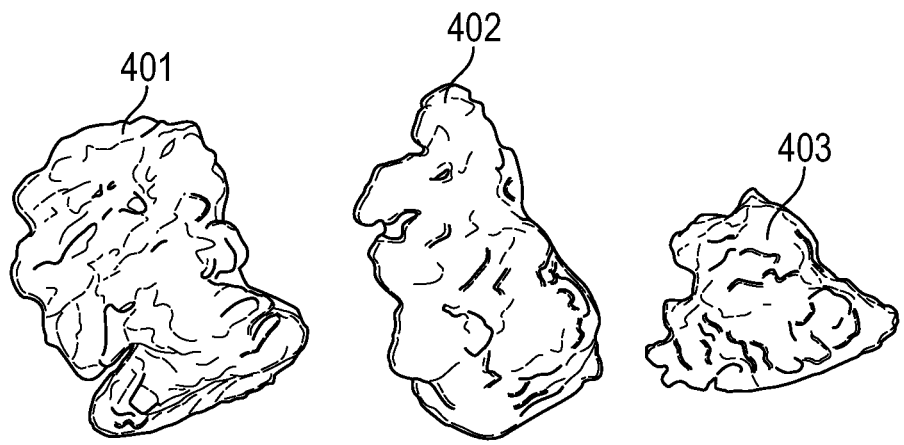
FIGS. 4A-4C illustrate a plurality of example morphology-specific occluder devices for use in the example system illustrated in FIG. 1.
Figure 4B:
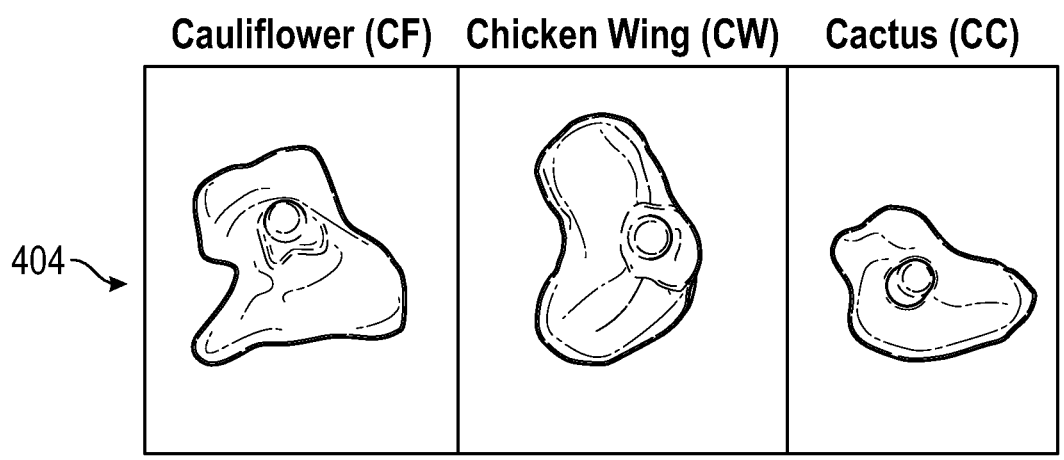
Figure 4C:
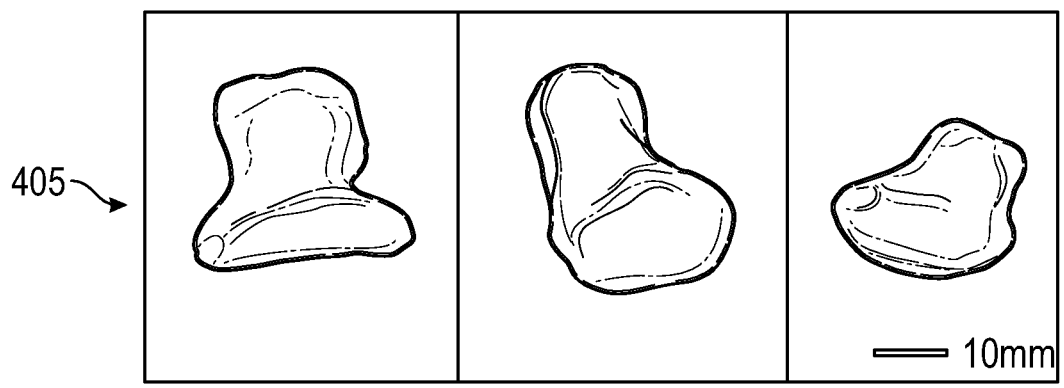

FIGS. 4A-4C illustrate a plurality of example MSO devices 102 for different morphology classes. Referring to FIG. 4A, the morphology 401 is classified into the cauliflower class. The morphology 402 is classified into the chicken wing class. The morphology 403 is classified into the cactus class. The row 404 (FIG. 4B) and row 405 (FIG. 4C) illustrate different views of a class-specific MSO device 102 corresponding to the respective morphologies 401 (cauliflower class, left pane of FIGS. 4B and 4C), 402 (chicken wing class, middle pane of FIGS. 4B and 4C), and 403 (cactus class, right pane of FIGS. 4B and 4C) under which they are listed.

FIGS. 5A-6D illustrate example methods for implanting a MSO device 102. The MSO device 102 can be deployed via a number of procedures. In one example, the MSO device 102 can be deployed via a transcatheter method where the MSO device 102 is inflated from the ostium of the LAA 108. In another example, the MSO device 102 can be deployed surgically and inflated from the distal end of the LAA 108.

Figure 5A:
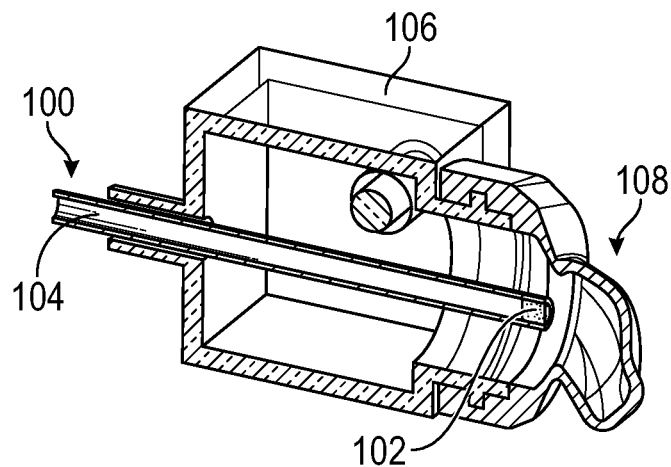
Figure 5B:
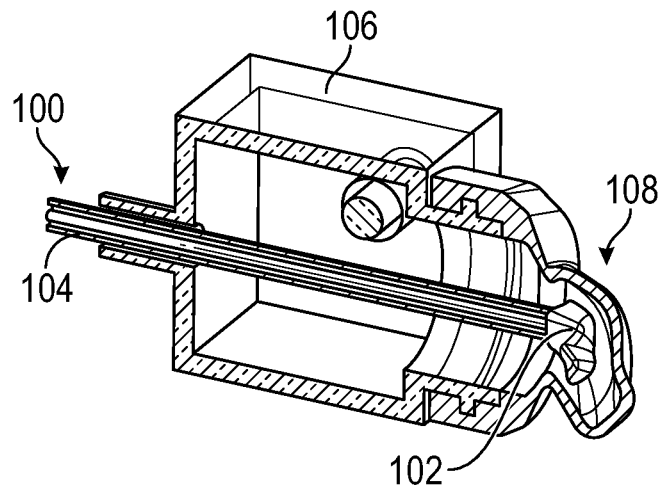
Figure 5C:
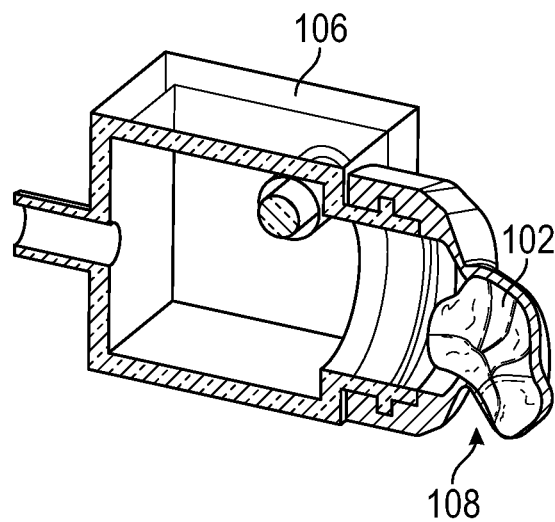

FIGS. 5A-5C illustrate an example occluder system 100 during the different stages of a transcatheter deployment. The occluder system 100 includes the MSO device 102. The occluder system 100 also includes a catheter through which the MSO device 102 is deployed. For illustrative purposes, in FIGS. 5A-5C the MSO device 102 is deployed into an in vitro testing system 106. The in vitro testing system 106 includes an artificial LAA 108. While illustrated in relation to the in vitro testing system 106, the occluder system 100 described herein is also configured to in vivo testing. For example, the occluder system 100 described herein can be used to occlude the LAA of a patient.

FIG. 5A illustrates the MSO device 102 contained within the catheter 104. The MSO device 102 can be fully contained within the catheter 104 in an undeployed state during the procedure to snake the tip of the catheter 104 from an insertion site (e.g., near the patient's groin) to the patient's left atrium. FIG. 5B illustrates the MSO device 102 after partial deployment into the artificial LAA 108 from the catheter 104. FIG. 5C illustrates the MSO device 102 fully deployed into the artificial LAA 108. As illustrated in FIG. 5C, the catheter 104 can be retracted from the artificial LAA 108 (or patient's heart) after deployment of the MSO device 102.

As illustrated in FIG. 5A, the MSO device 102 can be collapsible to fit within the catheter 104 and then expanded to fit within the patient's LAA. In some implementations, the MSO device 102 is expanded and deployed by infusing a fluid into the MSO device 102. The fluid used to fill the MSO device 102 can be cured (chemically, thermally, or with fiber coupled UV light) to ensure the deployed MSO device 102 retains its shape and stays lodged within the LAA. Furthermore, by solidifying the liquid, potential issues of balloon rupture will be reduced. As described above, the curable fluid is configured to have mechanical properties, such that the solidified MSO device 102 can accommodate the natural contractions of the left atrium and other portions of the heart. The MSO device 102 can be filled with epoxies, polyethylene glycol, collagen-based biocompatible polymeric gels, silicon, polyurethane, poly(methyl methacrylate), saline, self-expanding foam particles, or any combination thereof. The fluid (or other material) that fills and inflates the MSO device 102 can be referred to as an inflation fluid. In some implementations, a contrast agent or radiopaque material can be added to the filling or MSO device 102 to make the MSO device 102 visible to imaging devices. In some implementations, the fluids used to fill the MSO device 102 are stored in reservoirs that are coupled to the MSO device 102 via the catheter 104. The MSO device 102 can be filled by injecting the fluid from the reservoir and into the MSO device 102 via the lumen 122. In some implementations, the reservoir is a syringe.

FIGS. 6A-6D illustrate an example occluder system 100 during the stages of deployment from the distal end of the LAA 108. FIG. 6A illustrates a first step where a small incision is made in the LAA 108. The catheter 104, which during the initial steps contains the MSO device 102, attachment anchors 118, and a lumen 122, is inserted through the incision and into the LAA 108. As illustrated in FIG. 6A, purse string sutures 600 are made near where the catheter 104 is inserted into the LAA 108. FIG. 6B illustrates the retraction of the catheter 104. As the catheter 104 is retracted, the MSO device 102 is deployed into and remains within the LAA 108. FIG. 6C illustrates the filling (also referred to as the expansion or inflation) of the MSO device 102. The lumen 122 passes through the valve 112 and into the interior of the MSO device 102. The interior of the MSO device 102 can be filled with a fluid 602, such as a liquid epoxy. As the MSO device 102 is filled, the MSO device 102 expands to fill the volume of the LAA 108. After a predetermined amount of time, the fluid 602 cures and hardens. In some implementations, the MSO device 102 can be filled with a fluid or other material that does not cure or otherwise harden over time (e.g., saline). FIG. 6D illustrates the anchoring of the MSO device 102 to the LAA 108. The attachment anchors 118 can be sutures that are tied or otherwise coupled with the purse string sutures 600 placed in the LAA 108. The attachment anchors 118 can hold the MSO device 102 in place and within the LAA 108. In some implementations, the attachment anchors 118 can hold the MSO device 102 in place as the fluid filling the MSO device 102 cures. Once cured, the hardened shape of the MSO device 102 can hold the MSO device 102 within the LAA 108.

Figure 7:
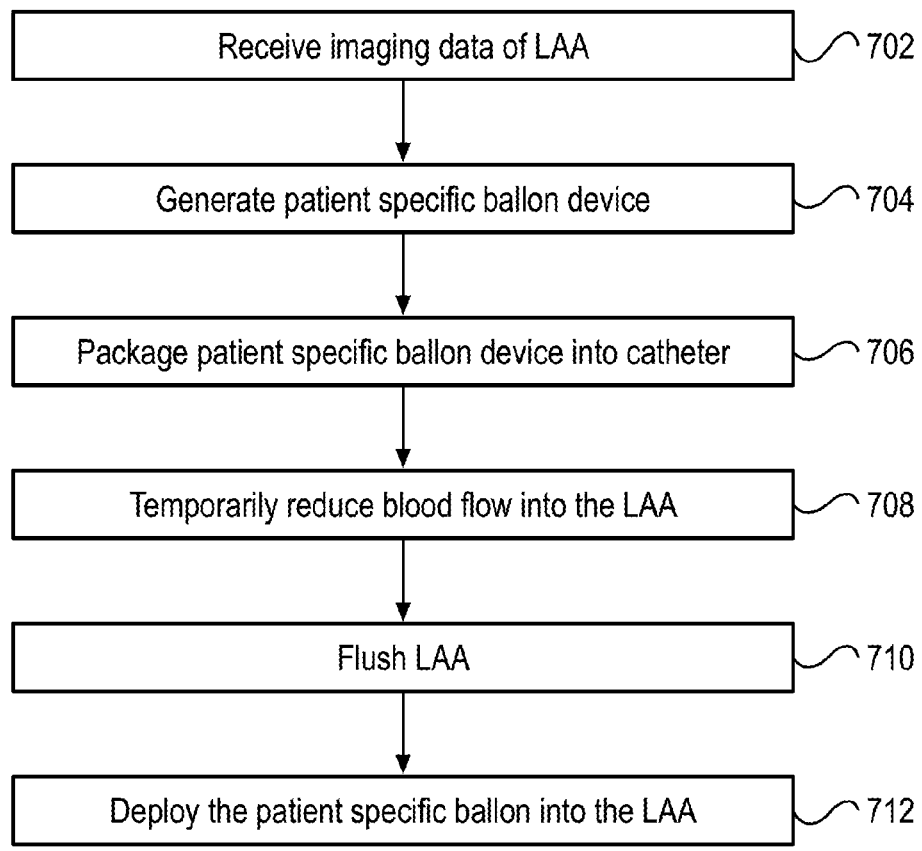
FIG. 7 illustrates a block diagram of an example method for deploying the occluder system illustrated in FIG. 1.

FIG. 7 illustrates a block diagram of an example method 700 for deploying a MSO device. The method 700 includes receiving imaging data of a patient's LAA (step 702). The method also includes generating a MSO device (step 704). The MSO device is packaged into a catheter (step 706). The method 700 also includes temporarily reducing blood flow to the patient's LAA (step 708). The LAA is then flushed (step 710). The MSO device is then deployed into the LAA (step 712).

The steps 702-706 can correspond to the manufacture of the MSO device 102. As set forth above, the method 700 includes receiving imaging data of a patient's LAA (step 702). In some implementations, the imaging data includes 3D imaging data received from a CT device. The imaging data can be processed to determine the volumetric shape of the patient's LAA. In some implementations, the patient's volumetric shape is matched to a template MSO device that includes a prefabricated volumetric shape. In some implementations, the MSO device is fabricated specifically for the patient. The shape of the MSO device manufactured specifically for the patient's anatomy can be referred to as a patient-specific morphology template.

The method 700 also includes generating the MSO device (step 704). In some implementations, the MSO device can be fabricated using rapid prototyping techniques, such as direct 3D printing of polyurethane materials. In other implementations, the MSO device is molding from 3D printed templates of silicone materials. In other implementations, the MSO device is manufactured using a subtractive 3D process. The MSO device can be manufactured from polyurethane, silicone, nylon, PET, or a combination thereof. Once the MSO device is manufactured, the MSO device is sterilized and packaged into a deployment catheter (step 706).

Figure 8A:
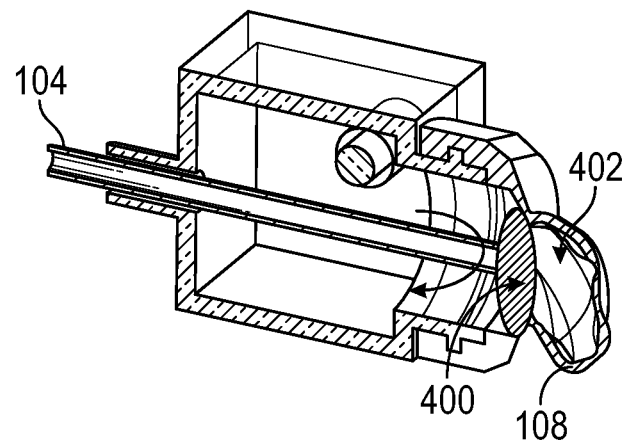
FIGS. 8A-8C illustrate the deployment of the occluder system according to the method illustrated in FIG. 7.

The steps 708-712 can correspond to the deployment of the MSO device. In some implementations, the steps 708-712 can be completed using an implantation method similar to the implantation method described in relation to FIGS. 6A-6D. Also referring to FIG. 8A, the method 700 includes temporarily reducing blood flow into the LAA (step 708). FIG. 8A illustrates the closure device during step 708 of method 700. FIG. 8A illustrates the use of an inflatable balloon 400 to reduce blood flow into the LAA. First, the tip of the occluder system 100 can be deployed near the LAA using a similar strategy to the Watchman closure device, by crossing the inter-atrial septum. The catheter 104 is preloaded with the MSO device and the inflatable balloon 400. In some implementations, the catheter 104 can include a hemostasis Y-adapter and a 3-way stopcock to control the infusion of the pressurizing fluid into the MSO device and inflatable balloon 400 and the deployment of a contrast dye.

As illustrated in FIG. 8A, first the tip of the catheter 104 is delivered toward the LAA. As illustrated in the FIG. 8A, the inflatable balloon 400 can be inflated to block blood flow between the LAA and the atrium. Initially, some blood 402 can be trapped within the LAA 108.

Figure 8B:
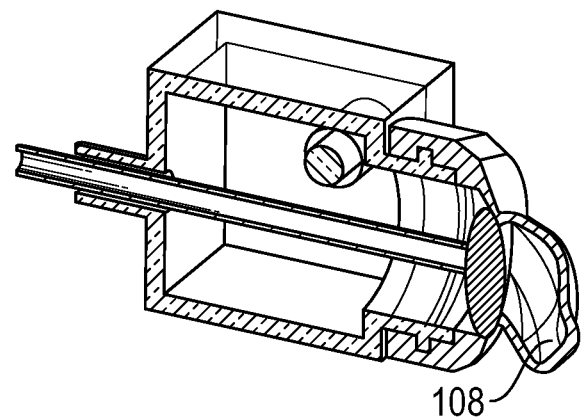

Referring to FIG. 7 and FIG. 8B, the method 700 can include flushing the LAA (step 710). FIG. 8B illustrates the LAA after the flushing according to step 710 of method 700. The LAA 108 can be flushed with a saline wash (or other medical grade fluid). The flushing can remove blood from within the LAA 108. The blood removed during the flushing of the LAA can be the blood trapped between the inflated balloon 400 and the walls of the LAA 108. Removing the blood can reduce the chances of blood being trapped in the LAA 108 and forming clots.

Figure 8C:
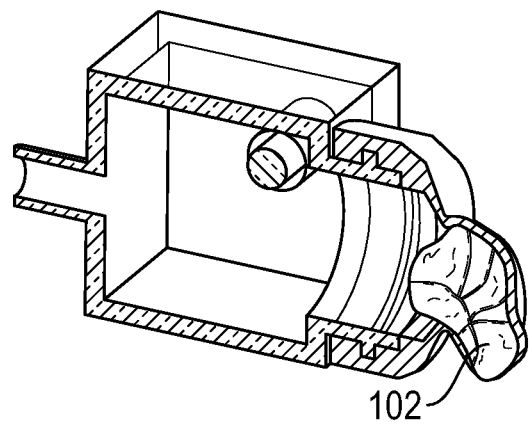

Referring to FIG. 7 and FIG. 8C, the method 700 can also include deploying the MSO device 102 into the LAA 108 (step 712). The MSO device 102 can be deployed into the LAA 108 from the tip of the catheter 104. In some implementations, the MSO device 102 can be deployed by flowing a fluid (such as a liquid or a gas) through the catheter 104 and into the MSO device 102. In some implementations, the fluid is a light, temperature, or time curable fluid. Once the fluid has filled the MSO device 102, the fluid can be cured such that the MSO device 102 maintains its patient-specific shape. FIG. 8C illustrates the deployed MSO device 102 after the retraction of the catheter 104.

In some implementations, during the deployment of the MSO device 102, it is important that the orientation and positioning be correct. To achieve this, radiopaque markers at the distal end of the catheter and the MSO device 102 can be used to visualize the catheter and/or MSO device 102 in situ. The markers can be designed such that the position (distance from LAA orifice) and orientation (angular alignment with LAA geometry) can be determined within an accuracy of about 1 mm using x-ray fluoroscopy techniques.

As used herein, the singular terms "a," "an," and "the" may include plural referents unless the context clearly dictates otherwise.

As used herein, relative terms, such as "above," "below," "up," "left," "right," "down," "top," "bottom," "vertical," "horizontal," "side," "higher," "lower," "upper," "over," "under," "inner," "interior," "outer," "exterior," "front," "back," "upwardly," "lower," "downwardly," "vertical," "vertically," "lateral," "laterally," and the like refer to an orientation of a set of components with respect to one another; this orientation is in accordance with the drawings, but is not required during manufacturing or use.

As used herein, the terms "connect," "connected," and "connection" refer to an operational coupling or linking. Connected components can be directly or indirectly coupled to one another, for example, through another set of components.

As used herein, the terms "approximately," "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, technique, or process to the objective, spirit, and scope of the present disclosure. All such modifications are intended to be within the scope of the claims appended hereto. While the techniques disclosed herein have been described with reference to particular operations performed in a particular order, it will be understood that these operations may be combined, sub-divided, or re-ordered to form an equivalent technique without departing from the teachings of the present disclosure. Accordingly, unless specifically indicated herein, the order and grouping of the operations are not limitations of the present disclosure.

What is claimed:

1. A method comprising:
   determining, based on a non-invasive medical image of an anatomy of a patient, a morphology class of an atrial appendage of the patient;
   selecting, based on the morphology class, a shape template from among a set of predetermined shape templates;
   obtaining an inflatable implant manufactured according to the selected shape template, the inflatable implant configured to have, in an inflated state, a volumetric shape corresponding to the shape template; and
   occluding the atrial appendage of the patient using the class specific inflatable implant with the volumetric shape.

2. The method of claim 1, wherein the set of predetermined shape templates comprises at least one of:
   a cactus shape template comprising a first main lobe that is between about 1 to 6 cm long and more than two secondary lobes that are each longer than about 0.5 cm;
   a chicken wing shape comprising a second main lobe that is about 1 to 6 cm long and one or more secondary lobes;
   a windsock shape comprising a third main lobe that is about 1 to 6 cm long, with the predetermined first angle being greater than about 100 degrees; or
   a cauliflower shape comprising a fourth main lobe and two secondary lobes, each secondary lobe being smaller than the fourth main lobe.

3. The method of claim 1, wherein the atrial appendage is a left atrial appendage (LAA) of the patient.

4. The method of claim 1, wherein occluding the atrial appendage of the patient comprises deploying the inflatable implant in the atrial appendage of the patient.

5. The method of claim 4, wherein deploying the inflatable implant comprises expanding the inflatable implant from a deflated state to the inflated state.

6. The method of claim 5, wherein expanding the inflatable implant comprises injecting an inflation fluid into the inflatable implant so as to fill an interior volume of the inflatable implant and thereby inflate the inflatable implant.

7. The method of claim 1, wherein the inflatable implant comprises a proximal lobe and a distal lobe, wherein the proximal lobe has a first volumetric shape and the distal lobe has a second volumetric shape different from the first volumetric shape.

8. The method of claim 1, wherein the inflatable implant is a component of an occluder device, and wherein the occluder device further comprises an anchor configured to secure the inflatable implant to the atrial appendage in which the implantable device is deployed.

9. The method of claim 1, wherein the medical image comprises a computed tomography image, an ultrasound image, or a magnetic resonance image of the anatomy of the patient.

10. The method of claim 1, further comprising imaging the anatomy of the patient using an imaging device.

11. The method of claim 10, wherein the imaging device is selected from the group consisting of a computed tomography device, an ultrasound device, and a magnetic resonance imaging device.

12. The method of claim 1, further comprising manufacturing the inflatable implant based on the selected shape template.

13. The method of claim 12, wherein manufacturing the inflatable implant comprises 3D-printing at least a portion of the inflatable implant.

14. The method of claim 1, wherein the inflatable implant comprises one or more surface features on a proximal lobe, a distal lobe, or both the proximal lobe and the distal lobe, to facilitate engagement of the device with the atrial appendage in which the implantable device is deployed, wherein the surface features include at least of a ridge, a protrusion, a barb, an anchor, or a needle.

15. The method of claim 1, wherein the anatomy of the patient comprises a heart of the patient, or a portion of the heart.

16. A method comprising:
   determining, based on a medical image of an anatomy of a patient, a morphology class of an atrial appendage of the patient;
   selecting, based on the morphology class, a shape template from among a set of predetermined shape templates;
   manufacturing an inflatable implant according to the selected shape template, the inflatable implant having, in an inflated state, a volumetric shape corresponding to the shape template.

17. The method of claim 16, wherein the set of predetermined shape templates comprises at least one of:
   a cactus shape template comprising a first main lobe that is between about 1 to 6 cm long and more than two secondary lobes that are each longer than about 0.5 cm;
   a chicken wing shape comprising a second main lobe that is about 1 to 6 cm long and one or more secondary lobes;
   a windsock shape comprising a third main lobe that is about 1 to 6 cm long, with the predetermined first angle being greater than about 100 degrees; or a cauliflower shape comprising a fourth main lobe and two secondary lobes, each secondary lobe being smaller than the fourth main lobe.

18. The method of claim 16, wherein the anatomy comprises a heart of the patient, and wherein the atrial appendage is a LAA of the patient.

19. The method of claim 16, further comprising imaging the anatomy of the patient using a non-invasive imaging device to generate the medical image of the anatomy.

20. The method of claim 16, further comprising occluding the atrial appendage of the patient using the inflatable implant manufactured according to the selected shape template.

* * * * *